United States Patent
Chai et al.

[11] Patent Number: 5,807,864
[45] Date of Patent: Sep. 15, 1998

[54] 2-THIOXO-TETRAHYDROPYRIMIDIN-4-ONE DERIVATIVES

[75] Inventors: Sie-Yearl Chai, Lawrenceville, N.J.; Hassan M. Elokdah, Yardley; Theodore S. Sulkowski, Wayne, both of Pa.

[73] Assignee: American Home Products Corporation, Madison, N.J.

[21] Appl. No.: 807,164

[22] Filed: Feb. 27, 1997

Related U.S. Application Data

[60] Provisional application No. 60/012,993 Mar. 7, 1996.

[51] Int. Cl.$^6$ .................... C07D 239/56; A61K 31/505
[52] U.S. Cl. .............................................. 514/274; 544/309
[58] Field of Search .............................. 544/309; 514/274

[56] References Cited

U.S. PATENT DOCUMENTS

| | | | |
|---|---|---|---|
| 4,588,729 | 5/1986 | Teranishi | 514/263 |
| 4,927,451 | 5/1990 | Brouwer | 71/92 |

FOREIGN PATENT DOCUMENTS

| | | | |
|---|---|---|---|
| 0103436 | 8/1983 | European Pat. Off. | C07D 239/22 |
| 55108858 | 8/1980 | Japan | C07D 239/54 |
| 63066173 | 9/1986 | Japan | C07D 239/22 |

OTHER PUBLICATIONS

Iwao, Chemical Abstracts, vol. 103, entry 178225 (1985).
Avaeva et al., Chemical Abstracts, vol. 88, entry 90023 (197).
Dembecki et al., vol. 85, entry 32949 (1976).

*Primary Examiner*—John M. Ford
*Attorney, Agent, or Firm*—R. F. Boswell, Jr.

[57] ABSTRACT

This invention relates to the use of 2-thioxotetrahydropyrimidin-4-one derivatives to increase HDL cholesterol concentration and as therapeutic compositions for treating atherosclerotic conditions such as dyslipoproteinemias and coronary heart disease. The compounds of this invention are represented by the formula:

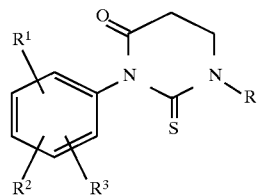

wherein:
  R is $C_1$–$C_6$ alkyl, $C_2$–$C_6$ alkenyl, or $C_2$–$C_6$ alkynyl; and $R^1$, $R^2$, and $R^3$ are independently hydrogen, halogen or lower alkyl.

14 Claims, No Drawings

2-THIOXO-TETRAHYDROPYRIMIDIN-4-ONE DERIVATIVES

This application claims priority to Provisional Application No. 60/012993 filed on Mar. 7, 1996.

FIELD OF THE INVENTION

This invention relates to the use of 2-thioxotetrahydropyrimidin-4-one derivatives to increase HDL cholesterol concentration and as therapeutic compositions for treating atherosclerotic conditions such as dyslipoproteinemias and coronary heart disease.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Russ et al., *Am. J. Med.,* 11 (1951) 480–493; Gofman et al, *Circulation,* 34 (1966) 679–697; Miller and Miller, *Lancet,* 1 (1975) 16–19; Gordon et al., *Circulation,* 79(1989) 8–15; Stampfer et al., *N. Engl. J. Med.,* 325 (1991) 373–381; Badimon et al., *Lab. Invest.,* 60(1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated level of some HDL particles in humans appears to be correlated to a decreased number of sites of stenosis in the coronary arteries of humans (Miller et al., *Br. Med. J.,* 282 (1981) 1741–1744).

There are several mechanisms by which HDL may protect against the progression of atherosclerosis. Studies in vitro have shown that HDL is capable of removing cholesterol from cells (Picardo et al., *Arteriosclerosis,* 6 (1986) 434–441). Data of this nature suggest that one antiatherogenic property of HDL may lie in its ability to deplete tissues of excess free cholesterol and eventually lead to the delivery of this cholesterol to the liver (Glomset, *J. Lipid Res.,* 9 (1968) 155–167). This has been supported by experiments showing efficient transfer of cholesterol from HDL to the liver (Glass et al., *Circulation,* 66 (*Suppl. II*) (1982) 102; MacKinnon et al., *J. Biol. Chem.,* 261 (1986) 2548–2552). In addition, HDL may serve as a reservoir in the circulation for apoproteins necessary for the rapid metabolism of triglyceride-rich lipoproteins (Grow and Fried, *J. Biol. Chem.,* 253 (1978) 1834–1841; Lagocki and Scanu, *J. Biol. Chem.,* 255 (1980) 3701–3706; Schaefer et al., *J. Lipid Res.,* 23 (1982) 1259–1273). Accordingly, agents which increase HDL cholesterol concentrations are useful as anti-atherosclerotic agents, particularly in the treatment of dyslipoproteinemias and coronary heart disease.

U.S. Pat. No. 4,927,451 claims benzoate substituted dihydrouracil derivatives (1) possessing herbicidal activity

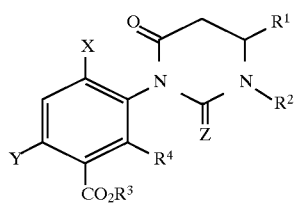

wherein $R^1$ is hydrogen, alkyl, cycloalkyl, alkenyl or $CF_3$; $R^2$ is alkyl, cycloalkyl, alkenyl, or aralkyl; $R^3$ is hydrogen or alkyl, $R^4$ is hydrogen or alkyl, X is halogen, Y is hydrogen, alkyl, or halogen; and Z is oxygen or sulfur.

U.S. Pat. No. 4,588,729 claims dihydrouracil derivatives of the following formula as anticonvulsants

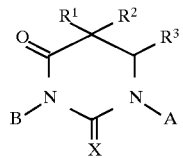

wherein X is oxygen or sulfur, $R^1$, $R^2$, and $R^3$ are independently hydrogen or alkyl, One of A and B is

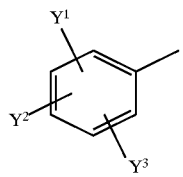

where $Y^1$, $Y^2$, and $Y^3$ are independently hydrogen, alkyl, nitro, amino, carboxyl, or halogen, and the other is

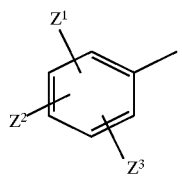

where $Z^1$, $Z^2$, and $Z^3$ are independently hydrogen, alkyl, halogen or $CF_3$.

The published European patent application EP 0 103 436 discloses the anticancer 5-perfluoroalkyl dihydrouracil derivatives below:

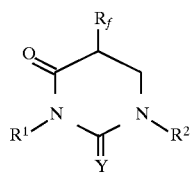

wherein Y is oxygen or sulfur; $R_f$ is perfluoroalkyl; and $R^1$ and $R^2$ are independently hydrogen, alkyl, cycloalkyl, aryl, aralkyl or a heterocyclic moiety.

The Japanese patent 55108858 discloses herbicidal utility for dihydrothiouracil derivatives of the formula:

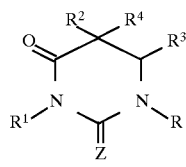

wherein Z is oxygen or sulfur; R and $R^1$ are independently alkyl, aryl, cyclohexyl or substituted phenyl; and $R^2$, $R^3$, and $R^4$ are independently hydrogen or alkyl.

Japanese patent 63066173 discloses a method of preparing uracil derivatives of the formula:

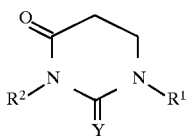

wherein $R^1$ is hydrogen, alkyl, aryl, or vinyl; $R^2$ is hydrogen, alkyl or aryl; and Y is O, S or NH. The compounds so prepared have antiviral, anticancer, antibacterial or insecticidal activity. Compounds of the present invention are not prepared by this process.

SUMMARY OF THE INVENTION

In accordance with this invention there is provided a group of substituted 2-thioxotetrahydropyrimidin-4-ones of the formula:

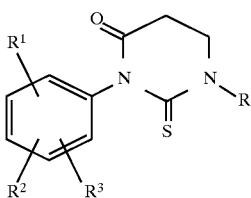

wherein:

R is $C_1$–$C_6$ alkyl, $C_2$–$C_6$ alkenyl, or $C_2$–$C_6$ alkynyl; and $R^1$, $R^2$, and $R^3$ are independently hydrogen, halogen or lower alkyl;
methods of increasing serum HDL and treating atherosclerosis and the conditions associated with atherosclerosis, and a pharmaceutical composition therefor.

The most preferred compounds of this invention based upon their potency and overall activity profile in the standard experimental test model are:

3-(2,6-dimethylphenyl)-1-ethyl-2-thioxotetrahydropyrimidin-4-one, 3-(4-chloro-2-methylphenyl)-1-ethyl-2-thioxotetrahydropyrimidin-4-one, 3-(2-chloro-6-methylphenyl)-1-ethyl-2-thioxotetrahydropyrimidin-4-one, 3-(5-chloro-2-methylphenyl)-1-ethyl-2-thioxotetrahydropyrimidin-4-one, 3-(2-ethyl-6-methylphenyl)-1-ethyl-2-thioxotetrahydropyrimidin-4-one, 3-(2-fluorophenyl)-1-ethyl-2-thioxotetrahydropyrimidin-4-one, 3-(2-isopropylphenyl)-1-ethyl-2-thioxotetrahydropyrimidin-4-one, 1-allyl-3-(2,6-dimethylphenyl)-2-thioxotetrahydropyrimidin-4-one, and 3-(2-ethyl-6-isopropylphenyl)-1-ethyl-2-thioxotetrahydropyrimidin-4-one.

DETAILED DESCRIPTION OF THE INVENTION

The compounds of the invention can be prepared readily according to the following reaction scheme or modification thereof using readily available starting materials, reagents and conventional synthetic procedures. It is also possible to make use of variants of these process steps, which in themselves are known to and well within the preparatory skill of the medicinal chemist. In the following reaction scheme (Scheme I) X is a halogen, and R is alkyl, alkenyl, or alkynyl as defined hereinabove.

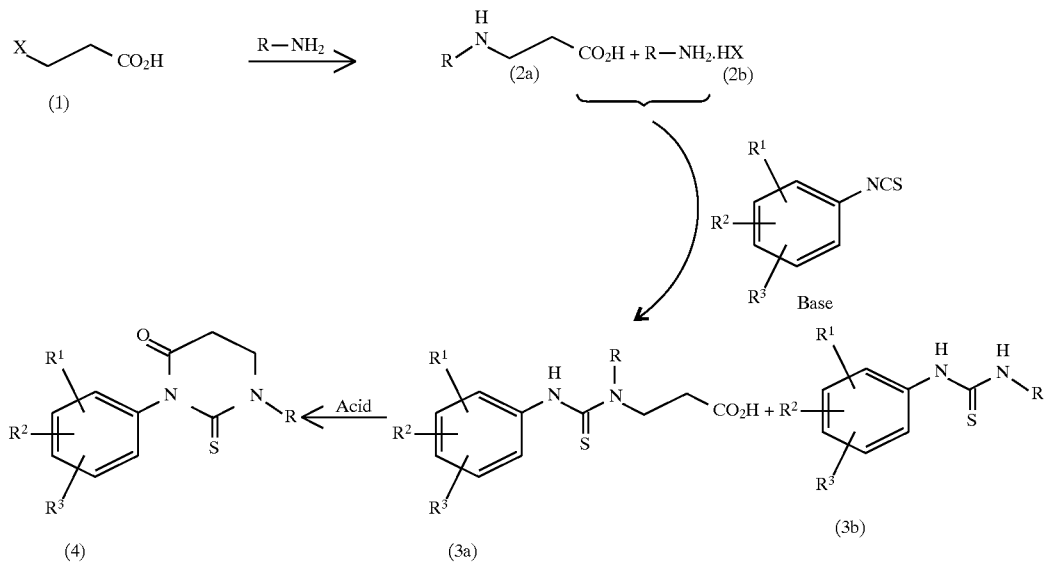

N-Substituted β-amino acids (2a) are prepared by reacting the corresponding β-halo acids (1) with the appropriate amine (excess). The reaction is carried out either neat or in water at ambient temperature for 18 hours. One equivalent of the amine scavenges the hydrohalide formed during the alkylation forming the amine hydrohalide (2b) as a side product. The N-alkyl β-amino acids (2a) and the amine hydrohalide (2b) are reacted with the isothiocyanates as crude product mixtures. Reactions of (2a) and (2b) with isothiocyanates are carried out in chloroform or methylene chloride in the presence of a base such as triethyl amine at reflux for 3 hours. The reaction affords a mixture of the thioureas (3a) and (3b). The thioureapropionic acid (3a) is extracted as its salt into aqueous base such as sodium hydroxide. Acidification affords the pure acid (3a). Cyclization of (3a) to the thiouracil (4) is accomplished either by refluxing in acetone containing 2% hydrochloric acid for 18 hours or by the action of trifluoro acetic anhydride at 0° C. for 3 hours followed by stirring at ambient temperature for 48 hours. Purification of (4) is achieved by crystallization from an appropriate solvent or by flash chromatography followed by crystallization.

The following examples are included for illustrative purposes only and should not be construed as limiting to this disclosure. Other methods of synthesis may be apparent to those skilled in the art. The various chemicals, reagents, and intermediates are either commercially available or readily prepared by persons skilled in the art of organic synthesis using standard literature procedures.

EXAMPLE 1

3-(2,6-Dimethylphenyl)-1-ethyl-2-thioxotetrahydropyrimidin-4-one

Step 1

3-Ethylaminopropionic acid

To a cooled solution of 500 mL aqueous ethylamine (70%), 3-chloropropionic acid (31.5 g) was added portionwise while stirring over 10 minutes. The mixture was stirred at ambient temperature for 18 hours. The mixture was then evaporated to a viscous oily residue (45 g). The product consisted of a 1:1 mixture of 3-ethylaminopropionic acid and ethylamine hydrochloride. This product mixture was used without further purification for the preparation of the title compound in step 2, and for preparation of the title compounds described in Example 2 through Example 8.

Step 2

3-[3-(2,6-Dimethylphenyl)-1-ethylthioureido] propionic acid

A mixture of 3-ethylaminopropionic acid (19.8 g), 2,6-dimethylphenyl-isothiocyanate (16.3 g), triethylamine (20 g) and methylene chloride (200 mL) was heated at reflux for 3 hours. The cooled reaction mixture was extracted with 1N NaOH (150 mL). The aqueous layer was separated and acidified with 2N HCl. The solid formed was collected by filtration. Recrystallization from ethanol afforded the title compound (11 g) as a white solid, m.p. 115°–118° C.

Anal. Calc'd. for $C_{14}H_{20}N_2O_2S$: C, 59.95; H, 7.19; N, 10.00.

Found: C, 59.57; H, 7.22; N, 9.93.

Mass spectrum (EI, M.$^+$) m/z 280.

Step 3

3-(2,6-Dimethylphenyl)-1-ethyl-2-thioxotetrahydropyrimidin-4-one

3-[3-(2,6-dimethylphenyl)-1-ethyl-thioureido]propionic acid (12 g) was dissolved in acetone (245 mL). Conc. HCl (5 mL) was added and the mixture was heated at reflux for 18 hours. The reaction mixture was evaporated to dryness. The residue was dissolved in methylene chloride (100 mL), and washed with 1N NaOH. The organic phase was dried over anhydrous magnesium sulfate, then evaporated to dryness. The solid was recrystallized from ethyl acetate to give the title compound (5.3 g) as a white solid, m.p. 124°–126° C.

Anal. Calc'd. for $C_{14}H_{18}N_2OS$: C, 64.09; H, 6.92; N, 10.68.

Found: C, 63.73; H, 6.79; N, 10.63.

Mass spectrum (EI, M.$^+$) m/z 262.

EXAMPLE 2

3-(4-Chloro-2-methylphenyl)-1-ethyl-2-thioxotetrahydropyrimidin-4-one

3-Ethylaminopropionic acid (19.8 g) was reacted with 4-chloro-2-methylphenylisothiocyanate (20 g), triethylamine (20 g), and methylene chloride (250 mL) according to the procedure described in step 2 of Example 1 to give 12 g of 3-[3-(4-chloro-2-methylphenyl)-1-ethyl-thioureido] propionic acid. The product (12 g) was dissolved in acetone (245 mL). Conc. HCl (5 mL) was added and the mixture was heated at reflux for 18 hours. The reaction mixture was evaporated to dryness. The residue was dissolved in methylene chloride (100 mL), and washed with 1N NaOH. The organic phase was dried over anhydrous magnesium sulfate, then evaporated to dryness. The solid was recrystallized from ethanol. The title compound (8 g) was obtained as a white solid., m.p. 133°–136° C.

Anal. Calc'd. for $C_{13}H_{15}N_2ClOS$: C, 55.15; H, 5.33; N, 9.88.

Found: C, 55.22; H, 5.35; N, 9.91.

Mass spectrum (EI, M.$^+$) m/z 282.

EXAMPLE 3

3-(2-Chloro-6-methylphenyl)-1-ethyl-2-thioxotetrahydropyrimidin-4-one

The title compound was prepared by the procedure described in Example 2 using 30 g of 2-chloro-6-methylphenyl-isothiocyanate, triethylamine (30 g), and methylene chloride (250 mL) to give 19 g of 3-[3-(2-chloro-6-methylphenyl)-1-ethylthioureido]propionic acid. A 13 g portion of this intermediate compound was used to obtain the title compound. Purification was achieved through crystallization from ethanol. The title compound (6.9 g) was obtained as a white solid., m.p. 141°–144° C.

Anal. Calc'd. for $C_{13}H_{15}N_2ClOS$: C, 55.15; H, 5.33; N, 9.88.

Found: C, 55.06; H, 5.34; N, 9.86.

Mass spectrum (EI, M.$^+$) m/z 282.

EXAMPLE 4

3-(5-Chloro-2-methylphenyl)-1-ethyl-2-thioxotetrahydropyrimidin-4-one

The title compound was prepared by the procedure described in Example 2 using 9.2 g of 5-chloro-2-methylphenyl-isothiocyanate, triethylamine (10 g), and methylene chloride (150 mL) to give 7.6 g of 3-[3-(5-chloro-2-methylphenyl)-1-ethylthioureido]propionic acid. A 7.0 g portion of this intermediate compound was used to obtain the title compound. Purification was achieved through crystallization from ethanol. The title compound (2.5 g) was obtained as a white solid., m.p. 142°–145° C.

Anal. Calc'd. for $C_{13}H_{15}N_2ClOS$: C, 55.21; H, 5.35; N, 9.91.

Found: C, 55.31; H, 5.32; N, 9.80.

Mass spectrum (EI, M.$^+$) m/z 282.

EXAMPLE 5

3-(2-Ethyl-6-isopropylphenyl)-1-ethyl-2-thioxotetrahydropyrimidin-4-one

The title compound was prepared by the procedure described in Example 2 using 21.5 g of 6-isopropyl-2- ethylphenyl-isothiocyanate, triethylamine (20 g), and methylene chloride (250 mL) to give 15 g of 3-[3-(6-isopropyl-2-ethylphenyl)-1-ethylthioureido]propionic acid. A 14 g portion of this intermediate was used to obtain the title compound. Purification was achieved through crystallization from hexane-ethyl acetate. The title compound (2.2 g) was obtained as a white solid., m.p. 129°–132° C.

Anal. Calc'd. for $C_{17}H_{24}N_2OS$: C, 67.07; H, 7.95; N, 9.20.

Found: C, 67.14; H, 7.96; N, 9.21.

Mass spectrum (EI, M.$^+$) m/z 304.

EXAMPLE 6

3-(2-Ethyl-6-methylphenyl)-1-ethyl-2-thioxotetrahydropyrimidin-4-one

The title compound was prepared by the procedure described in Example 2 using 20 g of 2-ethyl-6-methylphenyl-isothiocyanate, triethylamine (20 g), and methylene chloride (250 mL) to give 20.5 g of 3-[3-(2-ethyl-6-methylphenyl)-1-ethylthioureido]propionic acid. A 10 g portion of this intermediate was used to obtain the title compound. Purification was achieved through crystallization from hexane. The title compound (2.8 g) was obtained as a white solid., m.p. 74°–77° C.

Anal. Calc'd. for $C_{15}H_{20}N_2OS$: C, 65.18; H, 7.29; N, 10.14.

Found: C, 65.02; H, 7.33; N, 9.99.

Mass spectrum (EI, M.$^+$) m/z 276.

EXAMPLE 7

3-(2-Fluorophenyl)-1-ethyl-2-thioxotetrahydropyrimidin-4-one

The title compound was prepared by the procedure described in Example 2 using 20 g of 2-fluorophenyl-isothiocyanate, triethylamine (20 g), and methylene chloride (250 mL) to give 12.5 g of 3-[3-(2-fluorophenyl)-1-ethylthioureido]propionic acid. A 10 g portion of this intermediate was used to obtain the title compound. Purification was achieved through crystallization from hexane. The title compound (4.9 g) was obtained as a white solid., m.p. 101°–104° C.

Anal. Calc'd. for $C_{12}H_{12}N_2OS$: C, 57.12; H, 5.19; N, 11.10.

Found: C, 57.38; H, 5.05; N, 11.16.

Mass spectrum (EI, M.$^+$) m/z 252.

EXAMPLE 8

3-(2-Isopropylphenyl)-1-ethyl-2-thioxotetrahydropyrimidin-4-one

The title compound was prepared by the procedure described in Example 2 using 20 g of 2-isopropylphenyl-isothiocyanate, triethylamine (20 g), and methylene chloride (250 mL) to give 12.5 g of 3-[3-(2-isopropylphenyl)-1-ethyl-thioureido]propionic acid. An 11 g portion of this intermediate was used to obtain the title compound. Purification was achieved through crystallization from hexane. The title compound (4.6 g) was obtained as a white solid., m.p. 118°–122° C.

Anal. Calc'd. for $C_{15}H_{20}N_2OS$: C, 65.18; H, 7.29; N, 10.13.

Found: C, 65.29; H, 7.23; N, 10.10.

Mass spectrum (EI, M.$^+$) m/z 276.

EXAMPLE 9

1-Allyl-3-(2,6-dimethylphenyl)-2-thioxotetrahydropyrimidin-4-one

Step 1

3-Allylaminopropionic acid

To a cooled solution of 125 mL aqueous allylamine (60%), 3-chloropropionic acid (20 g) was added portionwise while stirring over 5 minutes. The mixture was stirred at ambient temperature for 72 hours. The mixture was then evaporated to a viscous oily residue (40 g). The product consisted of a 1:1 mixture of 3-allylaminopropionic acid and allylamine hydrochloride. This product mixture was used without further purification for the preparation of the title compound in step 2.

Step 2

3-[1-Allyl-3-(2,6-dimethylphenyl)-thioureido]propionic acid

A mixture of the 3-allylaminopropionic acid (21.9 g), 2,6-dimethylphenyl-isothiocyanate (19 g), triethylamine (20 g) and methylene chloride (200 mL) was heated at reflux for 3 hours. The cooled reaction mixture was extracted with 1N NaOH (150 mL). The aqueous layer was separated and acidified with 2N HCl. The solid was collected by filtration. 13.5 g of the title compound was obtained and used without further purification for the reaction in step 3.

Step 3

1-Allyl-3-(2,6-dimethylphenyl)-2-thioxotetrahydropyrimidin-4-one

To a cooled solution of trifluoroacetic anhydride (19.5 g), was added 9 g of 3-[1-allyl-3-(2,6-dimethylphenyl)-thioureido]propionic acid. The reaction mixture was stirred at 0°–5° C. for 4 hours, then stirred at ambient temperature for 72 hours. The reaction mixture was poured into ice-$H_2O$, basified with saturated $NaHCO_3$ solution, and extracted with methylene chloride (100 mL). The organic phase was dried over anhydrous magnesium sulfate, then evaporated to a gum. Purification was achieved by flash chromatography on silica gel (9:1=$CH_2Cl_2$:MeOH). Crystallization from hexane afforded the title compound (4.2 g) as a white solid, m.p. 88°–91° C.

Anal. Calc'd. for $C_{15}H_{18}N_2OS$: C, 65.66; H, 6.61; N, 10.21.

Found: C, 65.43; H, 6.55; N, 10.29.

Mass spectrum (EI, M.$^+$) m/z 274.

EXAMPLE 10

1-Propargyl-3-(2,6-dimethylphenyl)-2-thioxotetrahydropyrimidin-4-one

Following the procedures of Example 9, step 1 and substituting propargylamine for allylamine, 3-propargylaminopropionic acid is obtained is obtained. Following the procedures of steps 2 and 3 of Example 9 and substituting 3-propargylaminopropionic acid for 3-allylaminopropionic acid therein, the title compound is obtained.

Pharmacological Assay

The ability of the compounds of this invention to increase blood serum HDL levels was established by the following standard experimental procedure for determination of HDL cholesterol:

Male Sprague-Dawley rats weighing 200–225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005–0.1% of the total diet. Body weight and food consumption are recorded prior to diet administration and at termination. Typical doses of the test substances are 5–100 mg/kg/day.

At termination, blood is collected from anesthetized rats and the serum is separated by centrifugation. Total serum cholesterol is assayed using the Sigma Diagnostics enzymatic kit for the determination of cholesterol, Procedure No. 352, modified for use with ninety-six well microtiter plates. After reconstitution with water the reagent contains 300 U/l cholesterol oxidase, 100 U/l cholesterol esterase, 1000 U/l horse radish peroxidase, 0.3 mmoles/l 4-aminoantipyrine and 30.0 mmoles/l p-hydroxybenzenesulfonate in a pH 6.5 buffer. In the reaction cholesterol is oxidized to produce hydrogen peroxide which is used to form a quinoneimine dye. The concentration of dye formed is measured spectrophotometrically by absorbance at 490 nm after incubation at 25° C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) using a modification of the method of Kieft et al., *J. Lipid Res.*, 32 (1991) 859–866. A 25 μl sample of serum is injected onto Superose 12 and Superose 6 (Pharmacia), in series, with a column buffer of 0.05M Tris (2-amino-2-hydroxymethyl-1,3-propanediol) and 0.15M sodium chloride at a flow rate of 0.5 ml/min. The eluted sample is mixed on-line with Boehringer-Mannheim cholesterol reagent pumped at 0.2 ml/min. The combined eluents are mixed and incubated on-line through a knitted coil (Applied Biosciences) maintained at a temperature of 45° C. The eluent is monitored by measuring absorbance at 490 nm and gives a continuous absorbance signal proportional to the cholesterol concentration. The relative concentration of each lipoprotein class is calculated as the per cent of total absorbance. HDL cholesterol concentration in the serum is calculated as the per cent of total cholesterol as determined by FPLC multiplied by the total serum cholesterol concentration.

The compounds of the present invention increase HDL cholesterol concentrations as summarized in Table I:

TABLE I

| Compound of Example | Dose (mg/kg/day) | Duration of Treatment (days) | HDL Cholesterol Level Increase (%) |
|---|---|---|---|
| 1. | 100 | 8 | 184 |
| 2. | 100 | 8 | 126 |
| 3. | 100 | 8 | 199 |
| 4. | 100 | 8 | 76 |
| 5. | 100 | 8 | 34 |
| 6. | 100 | 8 | 60 |
| 7. | 100 | 8 | 72 |
| 8. | 100 | 8 | 108 |
| 9. | 100 | 8 | 83 |

Pharmaceutical Composition and Administration

This invention also provides pharmaceutical compositions comprised of 2-thioxotetrahydropyrimidin-4-ones either alone or in combination with pharmaceutically acceptable excipients. Such compositions are useful in the treatment of atherosclerotic conditions such as dyslipoproteinemias and coronary heart disease, in that they increase the blood serum high density lipoprotein concentration of mammals treated with the compounds.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid which is in admixture with the finely divided active ingredient. In tablets the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions which are sterile solutions or suspensions can be utilized by intramuscular, intraperitoneal or subcutaneous injection. In many instances a liquid composition form may be used instead of the preferred solid oral method of administration.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of HDL and the patients symptomatic relief analysis may be used to determine whether a larger dose is indicated. Based upon the data presented above, the projected daily dose for both human and veterinary use will be from about 25 to about 200 milligrams/kilogram per day, and more usually, from about 50 to about 100 milligrams/kilogram per day.

What is claimed is:

1. A method of increasing high density lipoprotein levels in blood in mammals in need of having high density lipoprotein levels raised which comprises administration thereto of a therapeutically effective amount of a compound of the formula:

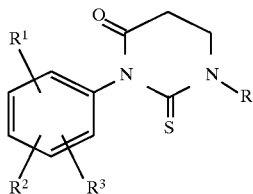

wherein:
R is $C_1$–$C_6$ alkyl, $C_2$–$C_6$ alkenyl, or $C_2$–$C_6$ alkynyl; and $R^1$, $R^2$, and $R^3$ are independently hydrogen, halogen or lower alkyl.

2. The method according to claim 1 wherein the compound used is 3-(2,6-dimethylphenyl)-1-ethyl-2-thioxotetrahydropyrimidin-4-one.

3. The method according to claim 1 wherein the compound used is 3-(4-chloro-2-methylphenyl)-1-ethyl-2-thioxotetrahydropyrimidin-4-one.

4. The method according to claim 1 wherein the compound used is 3-(2-chloro-6-methylphenyl)-1-ethyl-2-thioxotetrahydropyrimidin-4-one.

5. The method according to claim 1 wherein the compound used is 3-(5-chloro-2-methylphenyl)-1-ethyl-2-thioxotetrahydropyrimidin-4-one.

6. The method according to claim 1 wherein the compound used is 3-(2-ethyl-6-methylphenyl)-1-ethyl-2-thioxotetrahydropyrimidin-4-one.

7. The method according to claim 1 wherein the compound used is 3-(2-fluorophenyl)-1-ethyl-2-thioxotetrahydropyrimidin-4-one.

8. The method according to claim 1 wherein the compound used is 3-(2-isopropylphenyl)-1-ethyl-2-thioxotetrahydropyrimidin-4-one.

9. The method according to claim 1 wherein the compound used is 1-allyl-3-(2,6-dimethylphenyl)-2-thioxotetrahydropyrimidin-4-one.

10. The method according to claim 1 wherein the compound used is 3-(2-ethyl-6-isopropylphenyl)-1-ethyl-2-thioxotetrahydropyrimidin-4-one.

11. A compound according to the formula

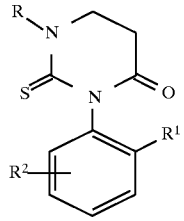

where R is ethyl or allyl, $R^1$ is methyl, ethyl, or isopropyl, and $R^2$ is 4-Cl, 5-Cl, 6-methyl, or 6-ethyl.

12. A compound according to claim 11 wherein when R is ethyl, the group

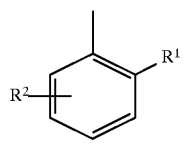

is selected from 2,6-dimethylphenyl, 4-chloro-2-methylphenyl, 5-chloro-2-methylphenyl, 2-ethyl-6methylphenyl, or 2ethyl-6-isopropylphenyl; and when R is allyl, the group

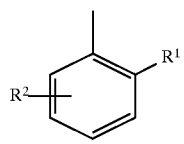

is 2,6-dimethylphenyl.

13. A compound according to claim 12 selected from:
3-(2,6-dimethylphenyl)-1-ethyl-2-thioxotetrahydropyrimidin-4-one,
3-(4-chloro-2-methylphenyl)-1-ethyl-2-thioxotetrahydropyrimidin-4-one,
3-(5-chloro-2-methylphenyl)-1-ethyl-2-thioxotetrahydropyrimidin-4-one,
3-(2-ethyl-6-methylphenyl)-1-ethyl-2-thioxotetrahydropyrimidin-4-one,
3-(2-ethyl-6-isopropylphenyl)-1-ethyl-2-thioxotetrahydropyrimidin-4-one, and
1-allyl-3-(2,6-dimethylphenyl-2-thioxotetrahydropyrimidin-4-one.

14. A pharmaceutical composition comprising a pharmaceutically acceptable carrier and an effective amount of a high density lipoprotein level elevating compound according to claim 11.

* * * * *